United States Patent
Vogt

(10) Patent No.: US 8,992,071 B2
(45) Date of Patent: Mar. 31, 2015

(54) MIXING DEVICE FOR MULTI-COMPONENT SYSTEMS

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

(*) Notice: Subject to any disclaimer, the term of this patent is extended or adjusted under 35 U.S.C. 154(b) by 67 days.

(21) Appl. No.: 13/873,664

(22) Filed: Apr. 30, 2013

(65) Prior Publication Data
US 2013/0294193 A1 Nov. 7, 2013

(30) Foreign Application Priority Data
May 7, 2012 (DE) .......................... 10 2012 008 815

(51) Int. Cl.
*B01F 15/02* (2006.01)
*A61C 5/06* (2006.01)
(Continued)

(52) U.S. Cl.
CPC ............. *B01F 15/0278* (2013.01); *A61C 5/064* (2013.01); *A61M 5/19* (2013.01); *B01F 5/0609* (2013.01); *B01F 13/0023* (2013.01);
(Continued)

(58) Field of Classification Search
CPC ................................................. B01F 15/0278
USPC ............. 366/162.2, 162.3, 168.2, 178.1, 280; 222/135, 145.5, 145.6
See application file for complete search history.

(56) References Cited

U.S. PATENT DOCUMENTS 1,417,965 A * 5/1922 Belcher ...................... 366/165.3
2,125,245 A  7/1938 McCray
(Continued)

FOREIGN PATENT DOCUMENTS

CH  669164 A5  2/1989
DE  3440893 A1  5/1986
(Continued)

OTHER PUBLICATIONS

English translation of the Notice of Reasons for Rejection issued in corresponding Japanese Application No. 2013-089710 dated May 20, 2014.

*Primary Examiner* — David Sorkin
(74) *Attorney, Agent, or Firm* — Norris McLaughlin & Marcus, P.A.

(57) ABSTRACT

A mixing device produces a multi-component mixture, in particular for medical applications, and has at least one first component and one second component, whereby the first component is a pasty fluid mass, whereby the mixing device has a housing having at least one first opening and a hollow body, whereby the hollow body has an internal space that contains the second component, and the mixing device has a feed plunger for expelling the second component from the internal space of the hollow body, whereby the hollow body has a thread and the feed plunger has a counter-thread that engages the thread of the hollow body, and the mixing device has a propulsion element that is arranged inside the housing, whereby the propulsion element converts a flow of the first component through the housing into a rotary motion, whereby the rotary motion of the propulsion element screws the feed plunger into the internal space of the hollow body, and whereby the second component can thus be extruded from the hollow space into the fluid flow of the first component.

20 Claims, 4 Drawing Sheets

Figure 1:
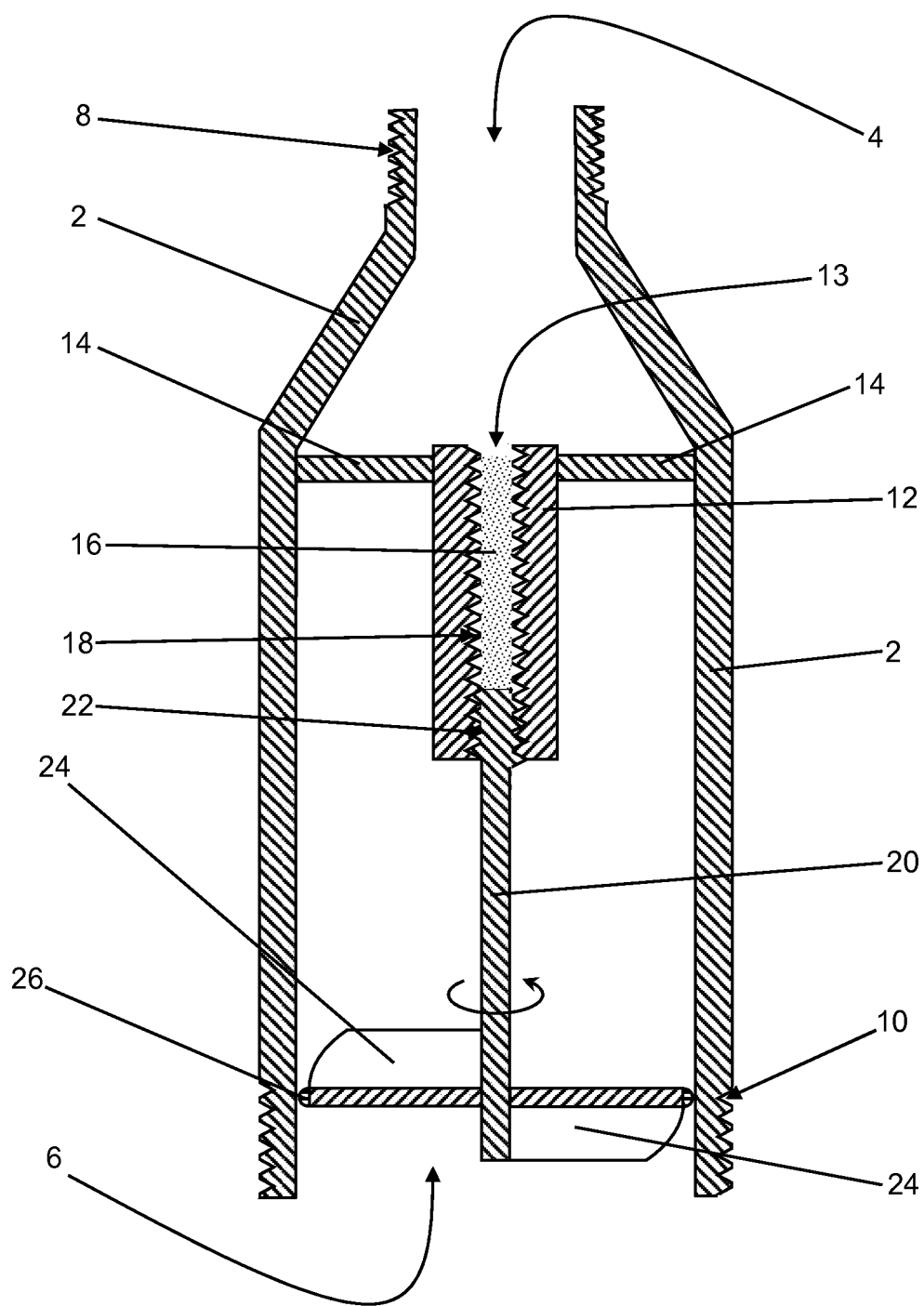

(51) Int. Cl.
*A61M 5/19* (2006.01)
*B01F 5/06* (2006.01)
*B01F 13/00* (2006.01)
*B01F 15/04* (2006.01)
*B01F 3/12* (2006.01)
*B05C 17/005* (2006.01)

(52) U.S. Cl.
CPC ............ *B01F15/047* (2013.01); *B01F 3/12* (2013.01); *A61C 5/068* (2013.01); *B05C 17/00563* (2013.01); *B01F 2215/0029* (2013.01); *B05C 17/00576* (2013.01)
USPC .................................. 366/162.2; 366/162.3

(56) References Cited

U.S. PATENT DOCUMENTS

| | | | | |
|---|---|---|---|---|
| 2,409,339 | A | * | 10/1946 | Ballard ................ 366/177.1 |
| 2,816,518 | A | * | 12/1957 | Daggett ................ 222/145.6 |
| 3,370,754 | A | | 2/1968 | Cook et al. |
| 3,417,971 | A | * | 12/1968 | Blank et al. .............. 366/196 |
| 3,848,507 | A | * | 11/1974 | Wisinski ...................... 86/1.1 |
| 4,068,830 | A | | 1/1978 | Gray |
| 4,690,306 | A | | 9/1987 | Staheli |
| 5,071,040 | A | | 12/1991 | Laptewicz, Jr. |
| 5,725,500 | A | * | 3/1998 | Micheler ........................ 604/82 |
| 5,968,018 | A | | 10/1999 | Freeman et al. |
| 6,367,962 | B1 | * | 4/2002 | Mizutani et al. ............ 366/189 |
| 8,167,835 | B2 | * | 5/2012 | Keller ............................. 604/89 |
| 2003/0179648 | A1 | | 9/2003 | Heusser et al. |
| 2009/0062808 | A1 | | 3/2009 | Wolf, II |

FOREIGN PATENT DOCUMENTS

| | | |
|---|---|---|
| DE | 10 2007 052 116 A1 | 4/2009 |
| DE | 10 2007 050 762 B3 | 5/2009 |
| DE | 10 2008 030 312 A1 | 1/2010 |
| DE | 10 2010 019 224 B3 | 10/2011 |
| DE | 10 2010 019 217 A1 | 11/2011 |
| DE | 10 2010 019 222 A1 | 11/2011 |
| EP | 0236129 A2 | 9/1987 |
| EP | 0261466 A1 | 3/1988 |
| EP | 0289882 A1 | 11/1988 |
| EP | 0294672 A1 | 12/1988 |
| EP | 0607102 A1 | 7/1994 |
| EP | 0664153 A1 | 7/1995 |
| EP | 0693437 A1 | 1/1996 |
| EP | 0787535 A1 | 8/1997 |
| EP | 2008707 A1 | 12/2008 |
| GB | 1188516 A | 4/1970 |
| JP | H 04 220259 | 8/1992 |
| JP | H 07 250897 | 10/1995 |
| JP | H 09 99034 | 4/1997 |
| JP | 2004 016707 | 1/2004 |
| WO | WO 2006/005206 A1 | 1/2006 |
| WO | WO 2006/045103 A2 | 4/2006 |

* cited by examiner

MIXING DEVICE FOR MULTI-COMPONENT SYSTEMS

The invention relates to mixing devices for producing a multi-component mixture, in particular for medical applications, comprising at least one first component and one second component, whereby the first component is a fluid mass, in particular a pasty mass, whereby the mixing device comprises a housing having at least one first opening and a hollow body, whereby the hollow body comprises an internal space containing the second component and the mixing device comprises a feed plunger for expelling the second component from the internal space of the hollow body.

The invention also relates to a cartridge system having a mixing device of this type and to an applicator having a cartridge system of this type. And lastly, the invention also relates to a method for producing a multi-component mixture, in particular using a mixing device of this type.

Mixing devices for mixing and, if applicable, applying a mixable material can consist of multiple individual parts and are to ensure that the two components are mixed thoroughly at the desired mixing ratios.

Basically, reactive pasty two-component systems are very common in technology for olefins for radical polymerisation, epoxy resins, and silicones and are produced in large quantities as adhesives and sealants for use in industry, crafts, and home improvement. Reactive pasty two-component systems are also common in dental technology.

Reactive pasty two- or multi-component systems must be stored separately after their production and until their application in order to prevent premature, inadvertent reactions of the components. Cartridge systems for the application of pasty two- or multi-component systems have been known for a long time. The following documents are cited for exemplary purposes, CH 669 164 A5, EP 0 607 102 A1, EP 0 236 129 A2, DE 3 440 893 A1, U.S. Pat. No. 4,690,306 A, US 2009/062808 A1, EP 0 787 535 A1, WO 2006/005 206 A1, EP 0 693 437 A1, EP 0 294 672 A, EP 0 261 466 A1, and EP 2 008 707 A1. After filling the cartridges with reactive pastes, the cartridges need to remain safely closed until their application. The pasty two- or multi-component systems are mixed right before their application, usually through the use of static mixers. The following documents are cited for exemplary purposes, GB 1,188,516 A, U.S. Pat. No. 2,125,245 A, U.S. Pat. No. 5,968,018 A, U.S. Pat. No. 4,068,830 A, US 2003/179648 A1, EP 1 799 335 A1, EP 0 664 153 A1, and EP 0 289 882 A1. In this context, mobile plungers, which are also used to dispense the cartridge content, usually seal the cartridge floors.

The backside of the cartridges is usually closed by mobile plungers that are designed for expelling the pastes during application. In the case of humidity- and air-sensitive pastes, aluminium cartridges may be used that are closed by plastic plungers and over which aluminium cylinders that are closed on one side are pressed in for sealing purposes. During the application of the pastes, the aluminium cylinder having one closed side is moved jointly with the plunger towards the front in the direction of the cartridge head through the action of cartridge applicator guns and the paste is expelled in the process. However, any contact of paste and aluminium surfaces may be problematic in medical applications.

Currently, so-called side-by-side cartridges and coaxial cartridges are commonly used as the technology for storage of reactive two-component paste systems. In this context, both pastes, which are stable by themselves, are stored spatially separated in separate cartridges and are mixed with each other only upon application. Static mixers are often used for mixing. The curing reaction is initiated only upon the two pastes being mixed with each other.

Polymethylmethacrylate bone cements have been in use in medicine for decades for permanent mechanical fixation of total joint endoprostheses. They are based on powder-liquid systems. Recently, polymethylmethacrylate bone cements that are based on the use of cement pastes have been proposed as well (DE 10 2008 030 312 A1, DE 10 2007 052 116 A1). Pasty two-component polymethylmethacrylate bone cements systems have been proposed as well (DE 10 2007 050 762 A1).

With regard to the application of bone cements for fixation of total joint endoprostheses, it is always necessary to take into consideration that the OR staff is under time pressure during these surgeries. Therefore, as a matter of principle, cartridge systems for medical applications involving the application of pasty polymethylmethacrylate bone cements should be designed such that they are largely resistant to user errors and can be operated rapidly and safely even in stressful settings.

Two-component systems curing through radical polymerisation are basically designed such that one paste contains a radical initiator while the other paste contains at least one accelerator. Usually, only very low amounts of accelerator are needed to generate radicals for initiation of the radical polymerisation through the accelerator reacting with the initiator. In order to attain equal mixing ratios, the known side-by-side cartridges have approximately equal internal diameters, since homogeneous dispensation is not ensured in the case of a small cartridge. This means that only small amounts of accelerator are distributed throughout a relatively large volume of paste. The paste only serves as a carrier for the accelerator.

The two pastes, or components as it may be, for the multi-component mixture, one containing the initiator and the second containing the accelerator, are usually stored separately in different cartridges. The pastes are pushed from said cartridges in the direction of the cartridge head by means of feed plungers arranged therein. In this context, it is important that the pastes are pressed at the predetermined volume ratio from the cartridges into static mixers which are arranged on each cartridge head. The pastes (components) are mixed in the static mixers and the curing reaction commences. It is essential to the quality of the cured paste material to maintain the mutual volume ratio of the two pastes. Most often the volume ratio of the pastes is in the range of 1:1 to 1:10. The volume ratio is maintained not only through the dimensioning of the cartridges, but also through synchronous propulsion of the feed plungers in the cartridges. In terms of technical means, said synchronous propulsion is effected by the two feed plungers being connected to each other. In most two-components systems, the feed plungers are connected to a toothed rack that is moved towards the cartridge head either through manual force via actuating levers or through motors.

Moreover, it is also feasible to press cartridges out using compressed air. In this context, a feed plunger having two pestles on its outside is situated in the applicator. During extrusion, compressed air is applied to the feed plunger which is thus made to move towards the cartridge head. Since both pestles are connected to the feed plunger, they can move to the front towards the cartridge head only in synchronous manner.

It is important to synchronise the dispensing, since the viscosity of the pastes usually is not exactly the same. Accordingly, simply applying pressure from compressed air to non-synchronised feed plungers would only lead to the feed plunger of the lower viscosity paste being pressed more rapidly towards the cartridge head than the comparably higher viscosity paste. This would change the predetermined volume ratio. This would result in sub-optimally cured paste material.

Directly applying compressed gas from compressed gas conduits or conventional compressed gas cartridges, such as carbon dioxide cartridges, to the feed plungers would be advantageous in that very large forces would be made to act on the feed plunger(s), which would allow highly viscous pastes to be extruded as well, and the extrusion pressure, and thus the extrusion rate, could be controlled by means of simple valves without any need to have mechanical devices such as toothed racks or gears present. Applicators having compressed gas cartridges are known from documents DE 2010 019 222 A1 and DE 10 2010 019 224 B3.

A generic mixing device for mixing and applying a mixable material is known from DE 10 2010 019 217 A1. The mixing device comprises at least two cartridges and a mixing space that is connected to the cartridges through one opening each. The cartridges have feed plungers for expelling the starting components arranged in it. The feed plungers are pushed into the cartridges through application of a pressure and the components are thus extruded from the cartridges and mixed with each other.

One advantage of all known systems is that the systems have two cartridges and can therefore not be readily operated with compressed gas. Moreover, the cartridge containing the accelerator takes up an unnecessarily large volume since homogeneous dispensation and therefore homogeneous mixing can otherwise not be achieved.

It is the object of the present invention to overcome these and other disadvantages that have not been specified above. In particular, a mixing device is to be provided that can be operated even by means of gas pressure without any difficulties. A mixing device with low space needs would also be advantageous. The mixing device should be easy to operate and be as immune to interference during its use as possible.

It is another object of the invention to develop a cartridge system and/or a mixing device for mixing and dispensing polymethylmethacrylate bone cement paste that enables the use of just one polymethylmethacrylate bone cement paste which can nevertheless be cured using a redox initiator system made up of at least one initiator and one accelerator. For this purpose, a device having a minimised volume is to be provided that dispenses small, but defined quantities of accelerator or initiator when the cement paste is being extruded in such manner that the entire cement paste extruded from the cartridge is mixed with an always constant quantity of accelerator or initiator.

Said objects are met through a mixing device for producing a multi-component mixture, in particular for medical applications, comprising at least one first component and one second component, whereby the first component is a fluid mass, in particular a pasty mass, whereby the mixing device comprises a housing having at least one first opening and a hollow body, whereby the hollow body comprises an internal space that contains the second component, and the mixing device comprises a feed plunger for expelling the second component from the internal space of the hollow body, whereby the hollow body comprises a thread and the feed plunger comprises a counter-thread that engages the thread of the hollow body, and the mixing device comprises a propulsion element that is arranged inside the housing, whereby the propulsion element converts a flow of the first component through the housing into a rotary motion, whereby the rotary motion of the propulsion element screws the feed plunger into the internal space of the hollow body, and whereby the second component can thus be extruded from the hollow space into the fluid flow of the first component.

According to the invention, the first component preferably is a pasty mass, whereby the second component can preferably be a pasty mass as well. Both components preferably are components of medical cements.

In this context, the invention can provide the thread of the hollow body to be an internal thread and the counter-thread of the feed plunger to be an external thread that engages the internal thread of the hollow body, whereby the internal wall of the internal space is preferably formed by the internal thread.

Said design allows the functional internal structure of the mixing device to be designed to be more compact and thus the entire mixing device to be designed with smaller external dimensions. Moreover, the threads arranged on the inside of the hollow body cannot be affected by filling materials of the first component.

According to a preferred refinement, the invention can provide the hollow body to be connected firmly to the housing, preferably through fins, and the propulsion element to be connected firmly to the feed plunger or the feed plunger to be connected firmly to the housing, preferably through fins, and the propulsion element to be connected firmly to the hollow body.

In either case, the housing bears a part of the internal structure such that the feed plunger can be screwed into the hollow space of the hollow body.

Moreover, the invention can provide the feed plunger to be supported like in a bearing such that it can rotate with respect to the hollow body and to be supported like in a bearing such that it can rotate in longitudinal direction of the internal space of the hollow body.

Due to this measure, the internal structure of the mixing device according to the invention can be selected to be simple in design.

Moreover, the invention can provide the internal space of the hollow body to comprise two openings, whereby one opening is closed through the feed plunger and the other opening is preferably open in the direction of the fluid flow of the first component, whereby it is particularly preferred for the internal space of the hollow body to essentially be cylindrical in shape and the two openings to be arranged at the base surfaces of the cylindrical internal space.

The effect of said design is that the content of the hollow body, i.e. the second component, can be extruded very easily from the hollow space.

According to a particularly preferred embodiment of the mixing device, the propulsion element can be a conveyor screw or comprise at least two blades and/or a blade disc, whereby the blades and/or blade disc comprise(s) at least one surface that is inclined with respect to the fluid flow of the first component or, preferably, comprise(s) multiple surfaces that are inclined with respect to the fluid flow of the first component.

Said blades, propellers or turbine blades are particularly well-suited for driving the feed plunger or the hollow body.

In this context, the invention can provide the inclined surface or the inclined surfaces of the blades and/or blade disc to be inclined between 5° and 85°, preferably between 30° and 60°, particularly preferably by 45°, with respect to the fluid flow of the first component.

A refinement of the mixing device according to the invention provides contact points on the propulsion element that are situated on the outside with respect to the axis of rotation of the propulsion element, by means of which the propulsion element can be guided on the inside of the housing, whereby the housing is cylindrical on the inside at least in said region.

The contact points allow the propulsion element to be guided in the housing without being able to become lodged.

Preferably, the invention can also provide the multi-component mixture to be a two-component mixture, in particular a curing medical cement, whereby one component comprises an accelerator and the other component comprises an initiator, whereby the first component preferably comprises methacrylate monomers and polymers dissolved therein, and particularly preferably is a polymethylmethacrylate bone cement paste, and the second component comprises the initiator, in particular a radical initiator system.

Particularly well-suited starting components are available for said multi-component mixtures, in particular for the medical cements. Moreover, the compact design is particularly advantageous for manual use.

Moreover, the invention can provide that a cartridge can be connected or is fastened to the housing, preferably at a second opening of the housing, whereby the cartridge contains the first component and the cartridge comprises a plunger for expelling the first component from the cartridge and for generating the fluid flow of the first component through the housing, whereby the cartridge preferably can be or is connected to the housing by means of fastening means, particularly preferably by means of a thread, a bayonet closure or snap-in locking means.

If the cartridge is or can be connected firmly to the housing, the fluid flow of the first component can also be generated through the application of strong mechanical pressure to the plunger.

The invention can just as well provide that a dispensing tube can be connected or is fastened to the housing as an extension of the at least one opening such that the multi-component mixture can be dispensed through the dispensing tube, whereby it is preferred to have a static mixer for mixing the multi-component mixture arranged on the inside of the dispensing tube.

The dispensing tube improves the user-friendliness of the structure. The static mixer improves the mixing effect of the mixing device.

According to a refinement, the invention can provide the second component to be a solid that is tucked into the internal space of the hollow body and dissolves in the fluid flow of the first component.

Solids as second components are particularly easy to tuck into the hollow space. Moreover, solids cannot leak prematurely such that there is no need to have a valve or protective film on the opening of the hollow body through which the second component can be dispensed.

Moreover, the invention can provide at least regions of the hollow body to be arranged inside the housing, preferably the hollow body and the feed plunger to be arranged fully inside the housing such that the fluid flow of the first component can flow around both of them.

This attains a particularly simple and compact design. Moreover, the hollow body can thus not be damaged from outside and is not visible to the user.

Another preferred mixing device according to the invention is characterised in that screwing the feed plunger into the inside of the hollow body is associated with the volume of the internal space of the hollow body being reduced proportional to the revolution of the propulsion element and thus proportional to the revolution of the feed plunger with respect to the hollow body and is associated with the rotation rate of the feed plunger being proportional to the volume flow of the first component through the propulsion element.

The second component is thus being admixed to the first component in defined quantities. The correct mixing ratio is forced at all times.

It is particularly preferred according to the invention for the second component to be a thixotropic liquid.

According to another particularly preferred refinement, the invention can provide the counter-thread of the feed plunger in the starting position to be essentially, or preferably fully, covered through the thread of the hollow body. Especially if the counter-thread is an internal thread and the thread of the hollow body is an external thread, this prevents substances such as radiopaquer ($ZrO_2$ particles) from blocking the thread during the mixing process.

It is particularly advantageous for the opening through which the second component is extruded from the hollow body to be oriented in the direction of the fluid flow of the first component. This measure allows the mixing of the components to be particularly homogeneous and smooth-running.

It is particularly preferred according to the invention to provide a valve, in particular a lip valve or a protective membrane, at the opening through which the second component is extruded from the hollow body. These measures allow contamination of the second component to be prevented. Moreover, the content of the hollow body can be prevented from undesired desiccating.

The objects of the invention are also met through a cartridge system comprising a mixing device of this type, a cartridge that contains the first component and comprises a plunger for extruding the first component into the mixing device.

Moreover, the objects of the invention are met through an applicator comprising a cartridge system of this type, an operable valve, and a compressed gas cartridge, in particular a $CO_2$ cartridge for applying a gas pressure to the plunger of the cartridge.

Moreover, the objects of the invention are met through a method for producing a multi-component mixture, in particular using a mixing device of this type, in which a first component is being pressed into a housing and generates a fluid flow therein, whereby the fluid flow drives a propulsion element and makes it rotate, and whereby the rotating propulsion element screws a feed plunger into an internal space of a hollow body, whereby a second component is thus extruded from the inside of the hollow body into the fluid flow of the first component and mixes with the first component therein and the mixture is being extruded from the housing.

In this context, the invention can provide that the feed plunger being screwed into the internal space of the hollow body is associated with the volume of the internal space of the hollow body being reduced proportional to the revolution of the propulsion element and thus of the feed plunger with respect to the hollow body, and is associated with a rotation rate of the feed plunger being generated to be proportional to the volume flow of the first component through the propulsion element.

Using cartridge systems for sterile pasty medical products, there is a need for not only the pastes, but obviously the cartridges and secondary packaging means also to be provided in sterile form to the user. For example after aseptic filling of the previously sterilised cartridges, these may be transferred directly to sterile packaging means. Moreover, it may make sense for certain products to sterilise the surfaces of filled cartridges jointly with the packaging means after packaging is completed. Aside from gamma sterilisation, which cannot be used with paste systems that can be polymerised, there is the option to use ethylene oxide gas for sterilisation.

In the scope of the invention, the term, polymethylmethacrylate bone cement paste, shall be understood to mean, in particular, pasty preparations of at least one methacrylate monomer and a polymer dissolved therein and at least one component of a radical initiator system, whereby said pastes are present in maximally swelled condition and are stored in said maximal swelled condition until use.

By comparison, pasty cement doughs of conventional powder-liquid-type polymethylmethacrylate bone cements made from mixtures of cement powders and monomer liquids are more difficult to use. In said pasty cement dough, the polymer particles in the monomer liquid that are present in the cement powder keep swelling constantly while the radical polymerisation of the monomer is ongoing and the monomer is being consumed. Said pasty cement dough cures within just a few minutes and is therefore not suitable for storing.

The invention is based on the surprising finding that connecting a hollow body and a feed plunger situated therein by means of a thread allows a defined propulsion of the feed plunger to be attained if the feed plunger is screwed-in by means of a propulsion facility that is operated through the volume flow of the first component. The propulsion of the feed plunger is then a direct function of the strength of the volume flow of the first component through the housing, in which the propulsion facility is arranged. The feed plunger can thus extrude even small quantities of the second component from the hollow space of the hollow body and thus admix them to the first component. The desired mixing ratio is thus always attained by this means regardless of the pressure acting on the plunger of the cartridge containing the first component.

The invention allows a desired mixing ratio to be established even when the volume of the second component is significantly smaller than that of the first component.

The invention is particularly advantageous also in that the device according to the invention allows a gas pressure to act directly and, possibly, on one plunger only without extensive synchronisation, in the form of synchronised pestles or other mechanical devices, being required. The mixing device according to the invention is particularly advantageous also because it can be inserted onto a cartridge head or into a dispensing tube and thus is particularly compact.

Regarding the minimisation of production costs of a pasty polymethylacrylate bone cement, the use of the invention necessitates just one, rather than two, polymethylmethacrylate bone cement pastes to be produced and said just one paste can be filled into a simple inexpensive cartridge. According to the invention, these can be polymerised through redox initiation and then cured by means of a redox initiator system made up of at least one initiator and at least one accelerator just as reliably as with the known two-component paste systems.

Accordingly, a core advantage of the invention is that just a single cartridge having just one plunger needs to be pressed out through direct application of compressed gas. Accordingly, it is feasible to press said cartridges out using a simple applicator that contains a compressed gas cartridge. Applicators having and being designed for compressed gas cartridges are known from documents DE 2010 019 222 A1 and DE 10 2010 019 224 B3.

A polymethylmethacrylate cement paste made up of at least one monomer for radical polymerisation and a polymer dissolved therein and filling agents, if applicable, is presumed to contain either an initiator or an accelerator. Said cement paste can be filled into a simple cartridge, whereby the cartridge contains a dispensing plunger and a connector for a dispensing tube is situated at the cartridge head. Said one dispensing plunger can have compressed gas applied to it in simple manner and the paste can thus be pressed in the direction of the cartridge head.

In this context, a particularly simple implementation of a mixing device according to the invention can provide the mixing device to be arranged on the cartridge head or in the dispensing tube and/or, as the case may be, as part of the dispensing tube, in such manner that it is situated right in the volume flow of the paste when the paste is extruded and is rinsed by the flowing paste fully or partially. The mixing device can be made up of a cylindrical hollow body having an internal thread and of a cylinder having an external thread as feed plunger for this purpose. The hollow body contains the accelerator or initiator in a solid, semi-solid or liquid form. The hollow body has at least two openings. At least one opening is connected to the surroundings in fluid-communicating manner. The cylinder having an external thread engages, through its external thread, the internal thread of the hollow body and closes an opening of the hollow body. The cylinder is arranged such that it can be rotated with respect to the hollow body. The hollow body or the cylinder (the feed plunger) are fixed in place on the housing of the dispensing tube or on a separate wall.

Moreover, blades are situated on the hollow body or on the cylinder in such manner that these effect a relative rotational motion of the hollow body with respect to the cylinder when the cement paste flows around the device in the direction of the dispensing opening of the dispensing tube such that the cylinder is rotated into the hollow body by means of its external thread engaging the internal thread of the hollow body. This reduces the volume of the hollow space in the hollow body proportional to the revolutions of the cylinder with respect to the hollow body and the accelerator or initiator contained in the hollow space is pressed into the flowing cement paste proportional to the revolutions, and thus proportional to the volume of the cement paste that has been pressed out. Arranged downstream in the dispensing tube in the direction of the dispensing opening, the static mixer then mixes the accelerator or initiator with the flowing paste to homogeneity.

Accordingly, the object of the invention is also met through a cartridge system having a mixing device for polymethylmethacrylate bone cement paste comprising a cartridge having a dispensing plunger, a dispensing tube, and static mixer arranged in the dispensing tube, which is characterised in that
a) a device is arranged upstream of the cartridge head or in the dispensing tube in appropriate manner such that the device is situated directly in the volume flow of the polymethylmethacrylate bone cement paste and has the polymethylmethacrylate bone cement paste flow all around it when the polymethylmethacrylate bone cement paste is being pressed out;
b) the device is made up of a cylindrical hollow body having an internal thread and a cylinder as feed plunger comprising an external thread;
c) the hollow body contains the accelerator or initiator in a solid, semi-solid or liquid form;
d) the hollow body possesses at least two openings;
e) at least one opening of the hollow body connects the hollow space of the hollow body to the surroundings in fluid-communicating manner;
f) the cylinder having an external thread engages, through its external thread, the internal thread of the hollow body and closes an opening of the hollow body;
g) the cylinder is arranged such as to be rotatable with respect to the hollow body, whereby the hollow body or the cylinder is fixed in place on the dispensing tube or a wall; and h) in that blades are attached to the hollow body or to the cylinder in appropriate manner such that these effect a relative rotary motion of the hollow body with respect to the cylinder when the cement paste flows around the device in the direction of the dispensing opening of the dispensing tube, and in that the cylinder is rotated into the internal thread of the hollow body by means of its external thread being engaged, whereby the volume of the hollow space in the hollow body is reduced proportional to the revolutions of the cylinder with respect to the hollow body and the accelerator or initiator contained in the hollow space is pressed into the flowing cement paste proportional to the revolutions and thus proportional to the volume of the cement paste that has been pressed out.

The blades thus form the propulsion facility of the mixing device. The existing housing of the dispensing tube is used as housing in this context and/or, as the case may be, the housing of the mixing device is made up jointly with the housing of the dispensing tube. It is feasible just as well to utilise the housing of the cartridge for the first component as the housing of the mixing device, and/or make up the housing of the mixing device jointly with the housing of the cartridge.

The polymethylmethacrylate bone cement paste is situated in the closed cartridge before use. Closure can be effected by means of a stopper or suitable valves.

The hollow body filled with accelerator or initiator can either be incorporated into the separate dispensing tube prior to application or it can be inserted into the dispensing tube right before use of the polymethylmethacrylate bone cement paste.

The cartridge is opened right before use and the dispensing tube containing the static mixer and the device is connected to the opened cartridge. The connection can be effected by means of a screw connection or snap-in connection in this context. Once the opened cartridge is connected to the dispensing tube containing the device and the static mixer, the cartridge system is ready for use.

Conceivable accelerators at room temperature are liquid electron-rich aromatic amines, such as N,N-dimethyl-aniline and N,N-dimethyl-p-toluidine. These can be converted to a pasty consistency through thickening agents which prevents them from leaking from the hollow space of the device before use of the cement. According to the invention, the aromatic amine, N,N-bis-hydroxyethyl-p-toluidine, can be used particularly preferably since it has a pasty consistency at room temperature and can easily be plastically deformed and pressed out. Moreover, it dissolves quickly in methylmethacrylate and can therefore be mixed with bone cement paste without any difficulties.

Aside from this substance, other accelerators or accelerator combinations are conceivable as well. Accordingly, mixtures of liquid or viscous organic ammonium chlorides, such as, for example, trioctylmethylammoniumchloride (Aliquat 336) and heavy metals salts, such as copper(II) methacrylate, suspended or dissolved therein, are well-suited just as well. It is particularly advantageous to combine a viscous ammonium chloride and an also liquid heavy metal salt. Conceivable heavy metal salts that are liquid at room temperature are, in particular, 2-ethylhexanoates of heavy metals, whereby copper(II) 2-ethylhexanoate is particularly well-suited.

Aside from this substance, heavy metal salts are feasible as accelerators in the absence of ammonium chlorides as well. Moreover, reduction agents are well-suited as accelerators. Pertinent examples include thiourea and substituted thioureas.

Organic peroxides, such as diacylperoxides, dialkylperoxides, and hydroperoxides, are well-suited as initiators. Aside from these substances, substituted barbiturates are also conceivable as initiators. Pertinent examples include 1-cyclohexyl-5-ethyl-barbiturate and 5-butyl-barbiturate.

The invention can provide the hollow body to be fixed in place, by means of fins, in the dispensing tube or in a cylinder that is fastened on the cartridge head, whereby an opening of the hollow body is arranged in the direction of the dispensing opening of the dispensing tube, whereby blades that are inclined with respect to the longitudinal axis of the cylinder are arranged on the cylinder and the cylinder engages, through its external thread, the internal thread of the hollow space via an opening that is situated opposite from the dispensing opening of the dispensing tube.

Alternatively, the invention can provide the cylinder to be fixed in place, by means of fins, in the dispensing tube or in a cylinder that is fastened on the cartridge head, whereby the free cylinder end of the cylinder is arranged opposite to the direction of the dispensing opening of the dispensing tube, the hollow body engages, through its internal thread, the external thread of the cylinder, an opening of the hollow body is arranged in the direction of the dispensing opening of the dispensing tube parallel to the internal thread of the hollow body, and blades that are inclined with respect to the longitudinal axis of the hollow body are attached to the hollow body.

A method according to the invention for dispensing and mixing polymethylmethacrylate bone cement paste using a mixing device according to the invention can be implemented in that a plunger in a cartridge presses a polymethylmethacrylate bone cement paste in the direction of the cartridge head, whereby the polymethylmethacrylate bone cement paste flows around the device fully or partially and thus applies [pressure] to blades on a hollow body or on a cylinder (feed plunger) such that a relative rotary motion of the hollow body with respect to the cylinder is effected, whereby the cylinder is rotated into the hollow body since its external thread engages an internal thread of the hollow body, whereby the volume of the hollow space in the hollow body is reduced proportional to the revolution of the cylinder with respect to the hollow body, and the accelerator or initiator present in the hollow space is pressed into the flowing cement paste proportional to the revolutions and thus proportional to the cement paste volume that is pressed out.

Figure 2:
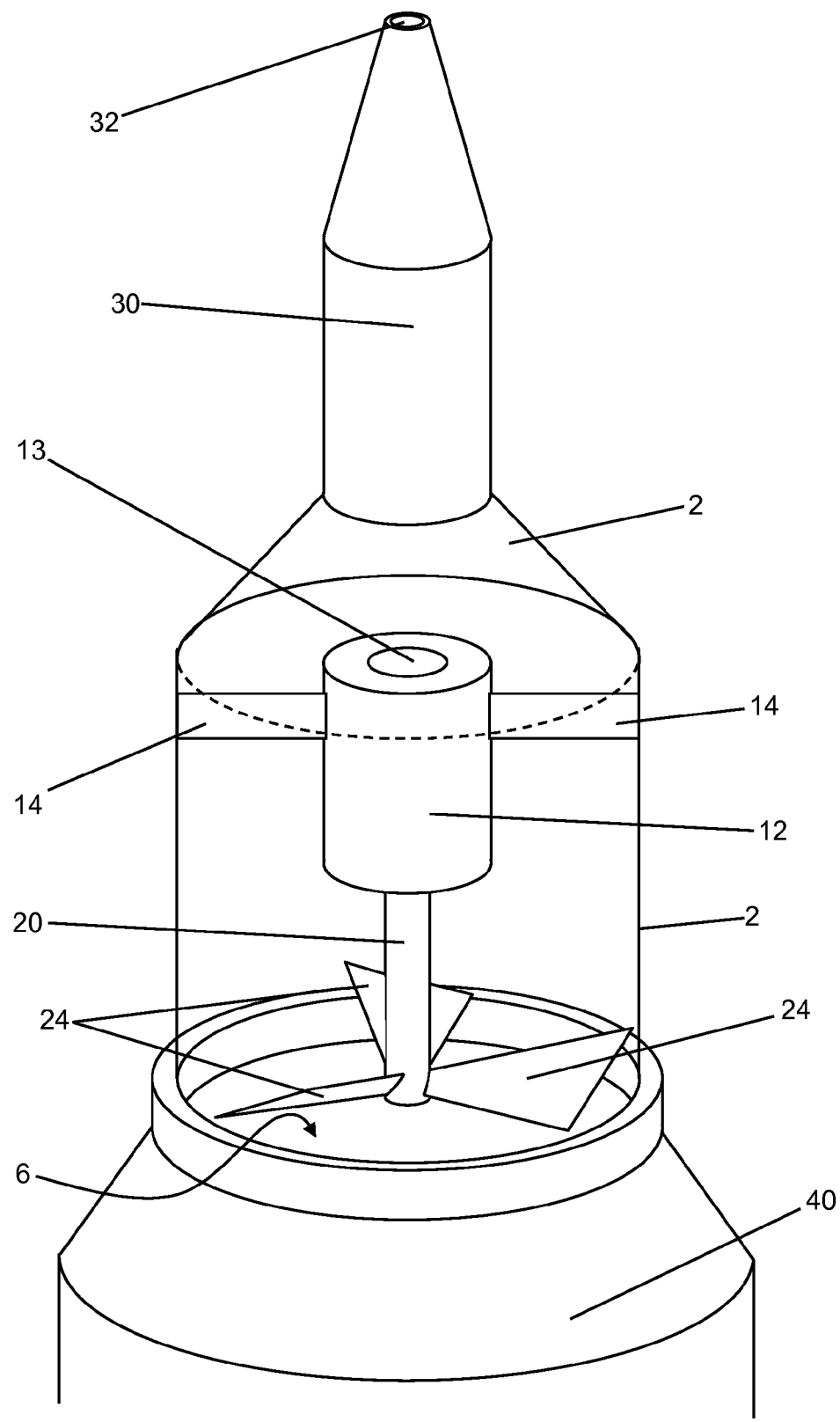
Figure 3:
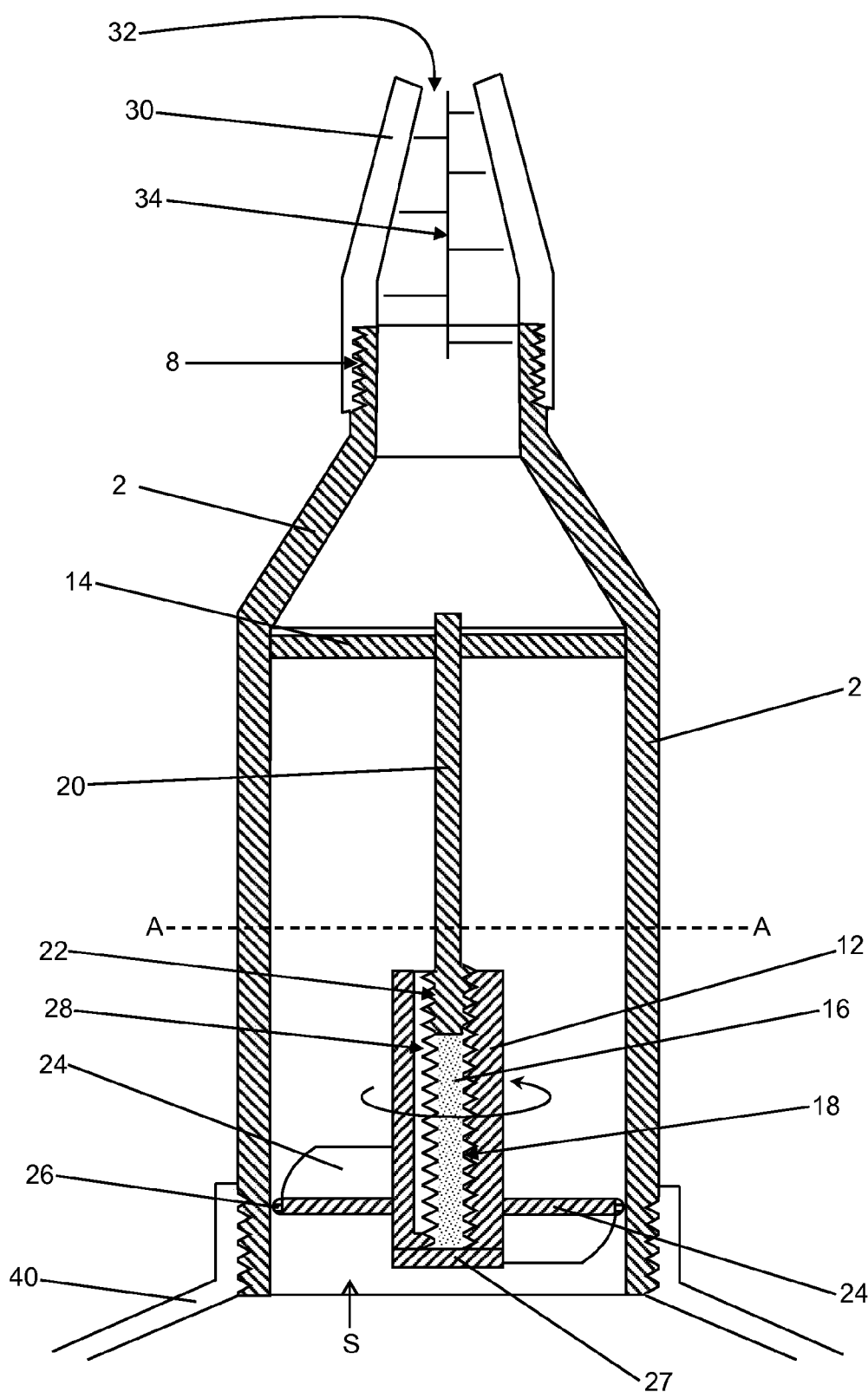
Figure 4:
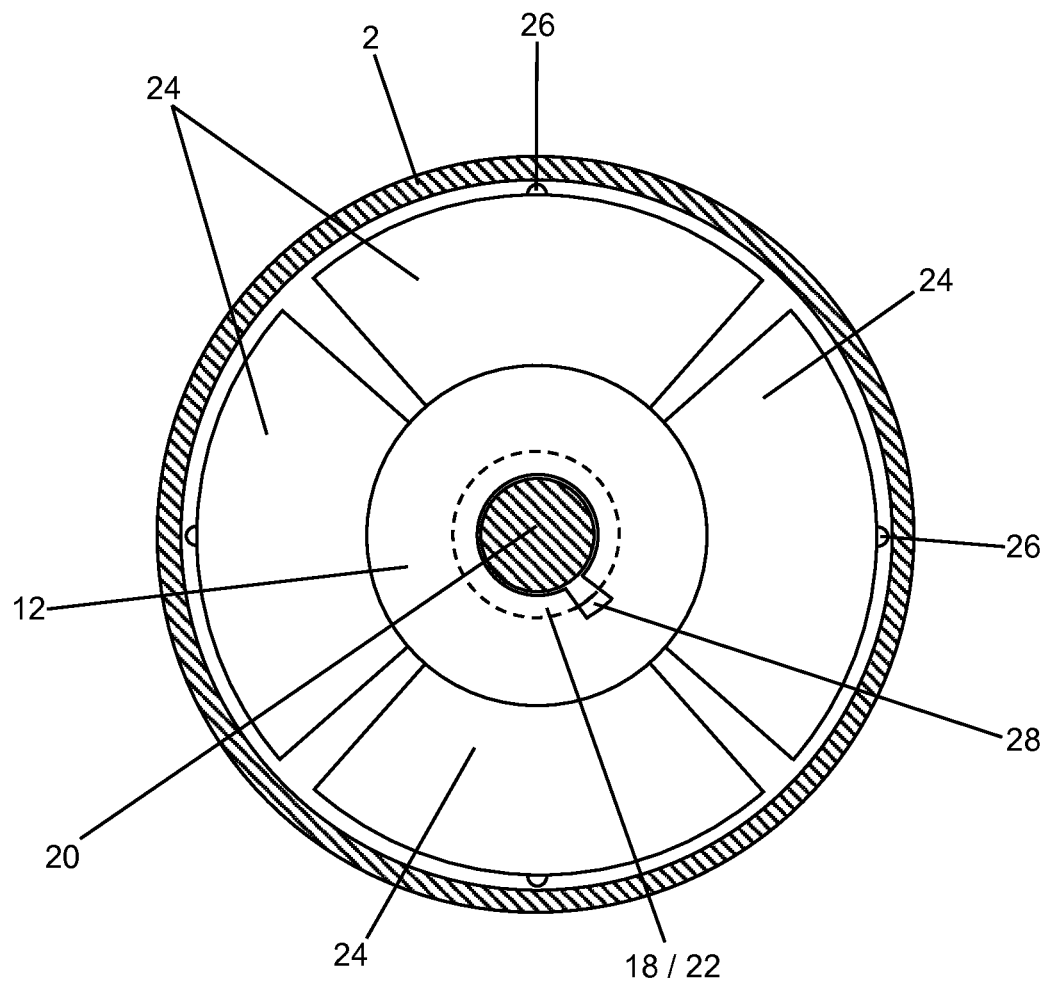

Exemplary embodiments of the invention shall be illustrated in the following on the basis of four schematic figures, though without limiting the scope of the invention. In the figures:

FIG. 1: shows a schematic cross-sectional view of a mixing device according to the invention;

FIG. 2: shows a schematic perspective view of a mixing device according to the invention having a transparent housing;

FIG. 3: shows a schematic cross-sectional view of a mixing device according to the invention having a dispensing tube and a cartridge attached to it; and FIG. 4: shows a schematic cross-sectional view along a perpendicular section A-A of the mixing device according to the invention according to FIG. 3.

FIG. 1 shows a schematic cross-sectional view of a mixing device according to the invention. The mixing device comprises a rotationally symmetrical housing 2 made of a thermoplastic material. The housing 2 is made up as a cylindrical tube that tapers in upward direction by means of a conical section and then is cylindrical in shape again. Openings 4, 6 are provided at both ends of the housing 2. The multi-component mixture (not shown) to be produced can be extruded through the upper opening 4, whereas a first component (not shown) is being pressed through the lower opening into the housing 2.

External threads 8, 10 are provided on both ends of the housing 2. A dispensing tube (not shown) having a static mixer can be screwed on at the upper thread 8. A cartridge (not shown) containing the first component is fastened to the lower thread 10. The cartridge comprises a plunger that can be used to press the first component into the housing. The cartridge and the dispensing tube can also be made of plastic material.

The inside of the housing 2 has a cylindrical hollow body 12 arranged in it that is arranged in the middle of the housing 2 by means of two or more fins 14. In the present case, the hollow body 12 is arranged as close as possible to the symmetry axis of the lower cylindrical region of the housing 2. A hollow space is provided on the inside of the hollow body 12 and is filled with the second component 16 and is open on both cover surfaces of the cylindrical hollow body 12. The second component 16 can be released to the surroundings of the hollow body 12 through the upper opening 13 of the hollow body 12. An internal thread 18 forms the internal wall of the hollow space.

The lower opening of the hollow body 12 is closed through a feed plunger 20. The feed plunger 20 comprises an external thread 22 that engages the internal thread 18 of the hollow body 12, which closes the lower opening of the hollow space. Accordingly, the feed plunger 20 can be screwed into the hollow space of the hollow body 12.

A propulsion element 24 that is firmly connected to the feed plunger 20 and can preferably be provided as the same part as the feed plunger 20 is arranged at the lower end of the feed plunger 20, which is formed mostly by means of a cylindrical rod that ends as a threaded rod. The propulsion element 24 is formed through multiple blades 24 which all have the same orientation with respect to the axis of rotation (symmetry axis) of the feed plunger 20, housing 2, and hollow body 12. The blades 24 are positioned slanted with respect to the lower opening 6 and thus with respect to the direction of flow of the first component being pressed into the housing 2. Accordingly, the propulsion element 24 has the same design as a propeller or a ship's propeller or, more exactly, like windmill blades or a turbine.

A fluid flowing into the housing 2 from below (the first component) rotates the propulsion element 24 as indicated by the arrow. The rotation screws the feed plunger 20 into the hollow space of the hollow body 12 and extrudes the second component 16 from the hollow body 12 into the fluid flow of the first component. The first component mixes with the second component 16 at this point and a two-component mixture is generated that is then extruded from the housing 2 through the upper opening 4.

In order to allow the propulsion element 24 some play but still define a position, contact points 26 in the form of semispheres are provided at the extreme tips of the blades 24 and ensure that each blade 24 has a point-like contact to the cylindrical internal wall of the housing 2, which positions the feed plunger 20 and the propulsion element.

FIG. 2 shows a schematic perspective view of an alternative mixing device according to the invention having a housing 2, in which the front wall of the housing 2 facing the observer is made transparent to allow a view into the inside of the mixing device. The front edge of the wall of the housing 2 is indicated through a dashed line. The housing 2 has a conical section (on the top in FIG. 2) and a cylindrical section (on the bottom in FIG. 2).

A cylindrical hollow body 12 having an upper opening 13 is arranged on the inside of the housing 2. Two fins 14 keep the hollow body 12 positioned in the middle of the housing 2. An internal thread (not shown) forms the internal wall of the cylindrical hollow body 12. A feed plunger 20, in the form of a rod having an external thread on its upper end, is screwed part-way into said internal thread. The threads are provided as left-hand threads in the present case, but right-hand threads can be used just as well. A propulsion element 24 having three inclined propeller blades 24 is arranged at the lower end of the feed plunger 20. If right-hand threads are to be used for the hollow body 12 and the feed plunger 20, the inclination of the blades 24 needs to be reversed A dispensing tube 30 is screwed-on at the top of the housing 2. An opening 32 through which the ready-made two-component mixture can be applied is provided at the tip of the dispensing tube 30. A static mixer improving the mixing of the two-component mixture can be provided on the inside of the dispensing tube 30.

A cartridge 40 containing the first component is fastened to the lower end of the housing 2. The housing 2 is open on top and bottom. The lower opening 6 can be seen below the propulsion element 24 and allows a view into the cartridge 40, whereas the upper opening is concealed through the dispensing tube 30. The cartridge 40 is designed for having the first component contained in it being pressed out through the opening 6 into the housing 2. This rotates the propeller 24 and screws the feed plunger 20 into the hollow body 12. This presses the content of the hollow body 12, i.e. the second component, into the flow of the first component that flows around the hollow body 12.

The mixture is then mixed more strongly through the static mixer in the dispensing tube 30 and can finally be applied through the opening 32 in the dispensing tube tip.

FIG. 3 shows a schematic cross-sectional view of another alternative mixing device according to the invention having a dispensing tube 30 and a cartridge 40 attached to it. Here, FIG. 4 shows a schematic cross-sectional view of the mixing device according to the invention according to FIG. 3 along a perpendicular section A-A that is shown in FIG. 3 as a dashed line.

Said embodiment is similar in design to the embodiments according to FIG. 1 or 2. The main difference being that fins 14 firmly connect a feed plunger 20, rather than the hollow body 12, to the housing 2. Accordingly, the propulsion element 24 is not firmly connected to the feed plunger 20, but rather to the hollow body 12. The feed plunger 20 is a cylinder made of plastic material having an external thread 22 that rotates into an internal thread 18 of the hollow body 12. Here, in contrast to the embodiments of the invention described in FIGS. 1 and 2, the propulsion element 24 does not drive and rotate the feed plunger 20, but rather the propulsion element 24 drives and rotates the hollow body 12. In both cases, the feed plunger 20 is being screwed into the hollow space of the hollow body 12.

Another difference between the mixing device design shown in FIGS. 3 and 4 and the designs according to FIGS. 1 and 2 is that the second component 16 contained in the hollow body 12 is not being extruded through the opening opposite from the feed plunger 20, since said opening is closed through a plate 27 in this case. Instead, longitudinal groove 28 through which the second component 16 is extruded in the direction of the feed plunger 20 out of the hollow body 12 is provided on the inside of the hollow body 12. The purpose of said design is to have the second component 16 extruded from the cartridge 40 in the flow direction of the first component indicated in FIG. 3 through arrow S.

There, the second component 16 from the hollow body 12 mixes with the first component from the cartridge 40. Like in the exemplary embodiments according to FIGS. 1 and 2, the mixture is then extruded past the fins 14 through a front opening of the housing 2. A dispensing tube 30 containing a static mixer 34 is screwed onto and fastened to the external thread 8 at the front opening of the housing 2. The static mixer 34 mixes the mixture before it is dispensed from the dispensing opening 32 at the dispensing tube tip.

Rather than producing only a two-component mixture, mixing devices according to the invention can just as well produce multi-component mixtures made up of multiple components. For example, the cartridge 40 or the hollow body 12 can be filled with more than one component that do not interfere with each other. Likewise, multiple hollow bodies 12 as shown having multiple feed plungers 20 and multiple propulsion elements 24 can be arranged behind each other or, alternatively, side by side in a longer housing 2.

The features of the invention disclosed in the preceding description and in the claims, figures, and exemplary embodiments, can be essential for the implementation of the various embodiments of the invention both alone and in any combination.

LIST OF REFERENCE NUMBERS

2 Housing
4 Front opening
6 Rear opening
8, 10 External thread
12 Hollow body
14 Fin
16 Second component
18 Internal thread
20 Feed plunger/cylinder rod
22 External thread
24 Propulsion element/blade
26 Contact point
27 Plate
28 Longitudinal groove
30 Dispensing tube
32 Opening/dispensing tube opening
34 Static mixer
40 Cartridge for the first component
A Cross-sectional plane of FIG. 4
S Fluid flow/direction of fluid flow of the first component

The invention claimed is:

1. A mixing device for producing a multi-component mixture comprising at least one first component and one second component (16), whereby the first component is a fluid mass or a pasty mass, whereby the mixing device comprises a housing (2) having at least one first opening (4) and a hollow body (12), whereby the hollow body (12) comprises an internal space containing the second component (16) and the mixing device comprises a feed plunger (20) for expelling the second component (16) from the internal space of the hollow body (12), wherein the hollow body (12) further comprises a thread (18) and the feed plunger (20) comprises a counter-thread (22) that engages the thread (18) of the hollow body (12), and the mixing device further comprises a propulsion element (24) that is arranged inside the housing (2), whereby the propulsion element (24) converts a flow (S) of the first component through the housing (2) into a rotary motion, whereby the rotary motion of the propulsion element (24) screws the feed plunger (20) into the internal space of the hollow body (12), and whereby the second component (16) is extrudable from the hollow space into the fluid flow of the first component.

2. The mixing device according to claim 1, wherein the thread (18) of the hollow body (12) is an internal thread (18) and the counter-thread (22) of the feed plunger (20) is an external thread (22) configured to engage the internal thread (18) of the hollow body (12), whereby an internal wall of the internal space is formed by the internal thread (18).

3. The mixing device according to claim 1, wherein
the hollow body (12) is connected to the housing (2), through fins (14), and the propulsion element (24) is connected to the feed plunger (20) or the feed plunger (20) is connected to the housing (2), through fins (14), and the propulsion element (24) is connected to the hollow body (12).

4. The mixing device according to claim 1, wherein the feed plunger (20) is supported such that the feed plunger is rotatable with respect to the hollow body (12) and is supported such that the feed plunger is rotatable in longitudinal direction of the internal space of the hollow body (12).

5. The mixing device according to claim 1, wherein the internal space of the hollow body (12) comprises two openings, whereby a first opening is closable through the fee plunger (20) and a second opening (13) is openable in a direction of the fluid flow (S) of the first component, whereby the internal space of the hollow body (12) is cylindrical in shape and the first and second openings are arranged at the base surfaces of the cylindrical internal space.

6. The mixing device according to claim 1, wherein the propulsion element (24) is a conveyor screw or comprises at least two blades (24) and/or a blade disc, whereby the blades (24) and/or blade disc comprise(s) at least one inclined surface that is inclined with respect to the fluid flow (S) of the first component or comprise(s) multiple inclined surfaces that are inclined with respect to the fluid flow (S) of the first component.

7. The mixing device according to claim 6, wherein the inclined surface or the inclined surfaces of the blades (24) and/or blade disc are inclined between 5° and 85° with respect to the fluid flow (S) of the first component.

8. The mixing device according to claim 1, further comprising contact points (26) on the propulsion element (24) that are situated on the outside with respect to the axis of rotation of the propulsion element (24), by means of which the propulsion element (24) is guidable on the inside of the housing (2), whereby the housing (2) is cylindrical on the inside at least in said region.

9. The mixing device according to claim 1, wherein the multi-component mixture is a two-component mixture, whereby a first component comprises an accelerator and a second component comprises an initiator.

10. The mixing device according to claim 1, further comprising
a cartridge (40) connected or fastened to the housing (2) at a second opening (6) of the housing (2), whereby the cartridge (40) contains the first component and the cartridge comprises (40) a plunger for expelling the first component from the cartridge (40) and for generating the fluid flow (S) of the first component through the housing (2), whereby the cartridge (40) is connectable to the housing (2) by fastening means (10).

11. The mixing device according to claim 1, further comprising a dispensing tube (30) connected or fastened to the housing (2) as an extension of the at least one opening (4) such that the multi-component mixture can be dispensed through the dispensing tube (30), whereby a static mixer (34) for mixing the multi-component mixture is arranged on the inside of the dispensing tube (30).

12. The mixing device according to claim 1, wherein the second component (16) is a solid tucked into the internal space of the hollow body (12) and dissolves in the fluid flow (S) of the first component.

13. The mixing device according to claim 1, further comprising at least regions of the hollow body (12) inside the hollow body (12) and the feed plunger (20) are arranged fully inside the housing (2) such that the fluid flow (S) of the first component can flow around both of them.

14. The mixing device according to claim 1, wherein screwing the feed plunger (20) into the inside of the hollow body (12) is associated with a volume of the internal space of the hollow body (12) being reduced proportional to a revolution of the propulsion element (24) and thus proportional to a revolution of the feed plunger (20) with respect to the hollow body (12) and is associated with a rotation rate of the feed plunger (20) being proportional to a volume flow of the first component through the propulsion element (24).

15. A cartridge system comprising the mixing device according to claim 1, a cartridge (40) that contains the first component and a plunger for extruding the first component into the mixing device.

16. An applicator comprising the cartridge system according to claim 15, an operable valve, and a compressed gas cartridge for applying a gas pressure to the plunger of the cartridge (40).

17. A method for producing a multi-component mixture, the method comprising:
provides the mixing device according to claim 1; and
pressing the first component into the housing (2) and generating the fluid flow (S) therein, whereby the fluid flow (S) drives the propulsion element (24) and makes it rotate, and whereby the rotating propulsion element (24) screws the feed plunger (20) into the internal space of the hollow body (12), whereby the second component (16) is thus extruded from the inside of the hollow body (12) into the fluid flow (S) of the first component and mixes with the first component therein and the mixture is being extruded from the housing (2).

18. The method according to claim 17, wherein
the feed plunger (20) being screwed into the internal space of the hollow body (12) is associated with a volume of the internal space of the hollow body (12) being reduced proportional to a revolution of the propulsion element (24) and thus of the feed plunger (20) with respect to the hollow body (12), and is associated with a rotation rate of the feed plunger (20) being generated to be proportional to a volume flow (S) of the first component through the propulsion element (24).

19. The mixing device according to claim 9, wherein whereby the first component is a polymethylmethacrylate bone cement paste, and the second component (16) comprises a radical initiator system.

20. The mixing device according to claim 10, wherein the fastening means is a thread (10), a bayonet closure or snap-in locking means.

* * * * *